US009867378B2

(12) United States Patent
Carrion Villarnovo et al.

(10) Patent No.: US 9,867,378 B2
(45) Date of Patent: Jan. 16, 2018

(54) BIOCONTROL OF PHYTOPARASITIC NEMATODES BY PAECILOMYCES

(71) Applicant: Instituto de Ecologia, A.C., Xalapa (MX)

(72) Inventors: Gloria Luz Laura Carrion Villarnovo, Xalapa (MX); Tania Isadora Hernández Leal, Xalapa (MX); José Daniel López Lima, Xalapa (MX); Ángel Enrique Nuñez Sanchez, Xalapa (MX)

(73) Assignee: Instituto de Ecologia, A.C., Xalapa (MX)

( * ) Notice: Subject to any disclaimer, the term of this patent is extended or adjusted under 35 U.S.C. 154(b) by 23 days.

(21) Appl. No.: 14/652,271

(22) PCT Filed: Dec. 13, 2013

(86) PCT No.: PCT/MX2013/000163
§ 371 (c)(1),
(2) Date: Jun. 15, 2015

(87) PCT Pub. No.: WO2014/092529
PCT Pub. Date: Jun. 19, 2014

(65) Prior Publication Data
US 2015/0342199 A1  Dec. 3, 2015

(30) Foreign Application Priority Data
Dec. 13, 2012 (MX) .................. MX/A/2012/014536

(51) Int. Cl.
*A01N 63/04* (2006.01)
*C12R 1/79* (2006.01)
*A01N 63/00* (2006.01)

(52) U.S. Cl.
CPC ............. *A01N 63/04* (2013.01); *A01N 63/00* (2013.01); *C12R 1/79* (2013.01)

(58) Field of Classification Search
None
See application file for complete search history.

(56) References Cited

U.S. PATENT DOCUMENTS

| 4,666,714 A | 5/1987 | Cayrol |
| 5,270,448 A | 12/1993 | Payne |
| 5,360,607 A | 11/1994 | Eyal et al. |
| 5,549,889 A | 8/1996 | Zuckerman et al. |
| 5,885,598 A | 3/1999 | Knauf et al. |
| 5,888,989 A | 3/1999 | Kern |
| 5,989,543 A | 11/1999 | Davide et al. |
| 6,294,712 B1 | 9/2001 | Kleine et al. |
| 7,435,411 B2 | 10/2008 | Park et al. |
| 7,576,261 B2 | 8/2009 | Hussey et al. |
| 2005/0008619 A1 | 1/2005 | Park et al. |
| 2009/0169518 A1 | 7/2009 | Antunes Franco |
| 2011/0162102 A1 | 6/2011 | Watanabe et al. |
| 2014/0079670 A1 | 3/2014 | Carrion Villamovo et al. |

FOREIGN PATENT DOCUMENTS

| CA | 2059642 | 8/1999 |
| CN | 1903014 A | 1/2007 |
| CN | 101081982 A | 12/2007 |
| CN | 101418264 A | 4/2009 |
| CN | 101422168 A | 5/2009 |
| CN | 101492323 A | 7/2009 |
| CN | 101518265 A | 9/2009 |
| DE | 102005024783 A1 | 12/2006 |
| MX | 2011004510 A | 1/2012 |
| WO | 91001642 A1 | 2/1991 |
| WO | 93002083 A1 | 2/1993 |
| WO | 9318170 A1 | 3/1999 |
| WO | 99059414 A1 | 11/1999 |
| WO | 03080838 A1 | 10/2003 |
| WO | 2012038476 A1 | 3/2012 |
| WO | 2012148251 A2 | 11/2012 |

OTHER PUBLICATIONS

Boag et al. "Nematodes and Nematophagous Fungi Associated with Cereal Fields and Permanent Pasture in Eastern Scotland", Crop Research, 1989, pp. 1-10, vol. 29, Issue 1.

*Primary Examiner* — Brian Gangle
(74) *Attorney, Agent, or Firm* — The Webb Law Firm

(57) ABSTRACT

Provided herein are methods of preventing/controlling phytoparasitic nematodes in migratory and sedentary endoparasites belonging to families Anguinidae, Aphelenchidae, Aphelenchoididae, Criconematidae, Dolichodoridae, Hemicycliophoridae, Heteroderidae, Hoplolaimidae, Iotonchidae, Neotylenchidae, Pratylenchidae, Sphaerulariidae, Tilenchidae, and Tylenchulidae: Suborder Tylenchina; Longidoridae: Suborder Dorylaimina; Trichodoridae: Suborder Diphtherophorina using *Paecilomyces carneus*. The compositions and processes disclosed herein are useful in the prevention and/or control and/or eradication of phytoparasitic nematodes that infect and/or infest the vast majority of cultures for animal and human consumption, while optimum conditions are created in the soil for improving crop yield, with the option of getting organic products.

9 Claims, 5 Drawing Sheets

SEQUENCE LISTING

<160> NUMBER OF SEQ ID NOS: 1

<210> SEQ ID NO 1
<211> LENGTH: 606
<212> TYPE: DNA
<213> ORGANISM: Paecilomyces carneus strain IE-418

<400> SEQUENCE: 1

```
gggatcatta ccgagtttac aactcccaaa cccctgtga acttatacca tttactgttg      60
cttcggcggg tcacggcccc ggggaaggac agcggtcgcc gtcaggcctc agctgcccgc     120
ccccggaaac aggcgcccgc cggggaactc aaaatattct gtatttcttt atctaatata     180
tactgtctga gtaaaaacta aaatgaatca aaactttcaa caacggatct cttggttctg     240
gcatcgatga agaacgcagc gaaatgcgat aagtaatgtg aattgcagaa ttcagtgaat     300
catcgaatct ttgaacgcac attgcgcccg ccagtattct ggcgggcatg cctgttcgag     360
cgtcatttca accctcaagt ccctgtgga ctcggtgttg gggaccggcg agacagccgc     420
ggatcttctt ccgcagcgag tcgccgcccc ccaaatgact tggcggcctc gtcgcggccc     480
tcctctgcgt agtatagcac acctcgcaac aggagcccgg cgaatggcca ctgccgtaaa     540
accccccaac tttttcagag ttgacctcga atcaggtagg aatacccgct gaacttaagc     600
atatca                                                              606
```

BIOCONTROL OF PHYTOPARASITIC NEMATODES BY PAECILOMYCES

CROSS-REFERENCE TO RELATED APPLICATIONS

This application is the United States national phase of International Application No. PCT/MX2013/000163 filed Dec. 13, 2013, and claims priority to Mexican Patent Application No. MX/a/2012/014536 filed Dec. 13, 2012, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 154952_ST25.txt. The size of the text file is 1,261 bytes, and the text file was created on Jun. 15, 2015.

FIELD OF THE INVENTION

The present invention relates to the use of *Paecilomyces carneus* for the prevention and/or control and/or eradication of phytoparasitic nematodes, migratory and sedentary endoparasites belonging to families Anguinidae, Aphelenchidae, Aphelenchoididae, Criconematidae, Dolichodoridae, Hemicycliophoridae, Heteroderidae, Hoplolaimidae, Iotonchidae, Neotylenchidae, Pratylenchidae, Sphaerulariidae, Tilenchidae, and Tylenchulidae: Suborder Tylenchina; Longidoridae: Suborder Dorylaimina; Trichodoridae: Suborder Diphtherophorina. The compositions and processes of the present invention are useful in the prevention and/or control and/or eradication of phytoparasitic nematodes that infect and/or infest the vast majority of cultures for animal and human consumption, while optimum conditions are created in the soil for improving crop yield, with the option of getting organic products.

BACKGROUND OF THE INVENTION

Pests are a biological factor that damages crops regardless of the region where they are. Damage caused by pests in the crops reduces the quality of the product and the amount of production, since they prevent plants to have an optimal development, and depending on the pest and the level of infestation, they can cause the death of the host.

Among the pests that affect the crops significantly, both in quality and in quantity, are the phytoparasitic nematodes, which are microscopic and depending on their life cycle they affect the plant in different ways. Some of the damages they cause to the crops are: withering, chlorosis, dwarfism, rickets, defoliation, lack of vigor, necrosis of the affected parts, resulting in a weak crop or the death thereof, and therefore production loss. In an effort to control pests that attack crops, farmers are in need to use chemical pesticides. Some of the disadvantages of them are the high risk posed when applied; the presence of the same in food products can result in damage to the health of consumers; also the alteration of pH and the contents of minerals in phytotoxic amounts as a consequence of the excessive application of chemical pesticides results in the loss of fertility of the soil; additionally they can have an effect in the quality of the product, as well as generating resistance to the chemical agents, which results in the need of make use of a larger amount thereof.

In the state of the art diverse methods for nematode control are described; among them are chemical methods, such as: use of 2R,5R-dihidroxymethil-2R,4R-dihidroxypyrrolidine (Pat. No. WO/1999/059414); a chemical agent with condensed formula $C_{27}H_{30}O_9$ (Pat. No. WO/1993/002083); use of fluopiram for nematode control (Pat. No. WO/2012/038476); fertilizer composition based on 1-70% potassium hypophosphite and ammonium phosphite, 1-307 boric fertilizer (Pat. No. CN101492323), among others.

On the other hand, there are biological methods where microorganisms are used for nematode control, these include: *Sphingobacterium* strain *spiritivorum* C-926 and *Corynobacterium paurometabolum* C-924 (Pat No. MX 250042); *Pasteuria* spp. (Pat No. MX 193344); fungi of the genus *Arthrobotrys* (Pat No. U.S. Pat. No. 4,666,714); *Bacillus thuringiensis* (Pat No. U.S. Pat. No. 5,270,448); *Streptomyces dicklowii* ATCC 55274 (Pat No. U.S. Pat. No. 5,549,889); fungus *Pochonia chlamydosporia* var. *chlamydosporia* (Pat No. US2009169518); *Verticillium chlamydosporium* CC 334168 (Pat No. WO/1991/001642), among others.

Another option is the combination of chemical compounds with biological agents, such as: *Buprofezina* and *Paecilomyces* sp. (U.S. Pat. No. 5,885,598); Silafluofen and/or Etofenprox with *Paecilomyces* sp. (U.S. Pat. No. 5,888,989), among others. Finally, there are methods that involve genetic modification for generating crops resistant to nematodes, such as those described in the following patent documents: GEP20002245, U.S. Pat. No. 6,294,712, U.S. Pat. No. 7,576,261, CN1903014, WO/2003/080838, among others.

The disadvantages that have been observed with chemical methods are those described above for the application of nematicides; as regarding the combination of chemical agents with biological agents, although sometimes is achieved to decrease the amount of the chemical agent, the disadvantages do not disappear; the genetic alteration of crops in order to create pest-resistant crops is an option that, besides having a high cost, poses a long-term risk for the consumers, since there is no certainty about the implications that the consumption of such products will have in the long term.

Nowadays, the biological methods are the most accepted and convenient, because they use microorganisms that are safe for the final consumer and help preserve the quality of soils, crops and thus of the final product.

Currently, the fungus of genus *Paecilomyces* spp. is used as nematicide, since it attacks nematodes effectively and without damaging crops. Patent documents U.S. Pat. No. 7,435,411 B2, CN101418264 and US 20050008619 describe the use of a composition containing *Paecilomyces lilacinus* for pest control in the soil; patent documents U.S. Pat. No. 5,989,543, CN101422168, DE102005024783, CN101081982, CA2059642, U.S. Pat. No. 5,360,607, U.S. Pat. No. 5,989,543, CN101518265 describe the use of *Paecilomyces lilacinus; Paecilomyces fumosoroseus, Paecilomyces lilacinus* 251, *Paecilomyces lilacinus* 252, *Paecilomyces lilacinus* 253, and *Paecilomyces lilacinus* 254; and *Paecilomyces cicadae* for nematode control and finally, in patent application MX/a/2011/004510 the use of *Paecilomyces carneus* strain IE-431 is described for the prevention and/or control and/or eradication of cyst-forming nematodes in solanaceous crops.

Among the highest-risk nematodes for crops are the gall-inducer nematodes of genus *Meloidogyne* spp., among others; root-lesion and root-borers, which are migratory endoparasites, including nematodes of genera *Ditylenchus* spp., *Pratylenchus* spp. and *Radopholus* spp., among others; and migratory and sedentary endoparasites, including nematodes of genera *Helicotylenchus* spp., *Criconemoides* spp., and *Xiphinema* spp., among others. The main crops affected by said nematodes are shown in Table 1:

TABLE 1

| Crops affected by nematodes | | | | | |
|---|---|---|---|---|---|
| Common name | Scientific name | *Meloidogyne* | *Pratylenchus* | *Helicotylenchus* | *Criconemoides* |
| Swiss chard | *Beta vulgaris* | | | | X |
| Agave | *Agave atrovirens* | X | X | X | X |
| Avocado | *Persea americana* | X | X | X | X |
| Garlic | *Allium sativum* | | X | | |
| Alfalfa | *Medicago sativa* | X | X | X | |
| Cotton | *Gossypium hirsutum* | X | X | | X |
| Sugar-apple | *Anona* spp. | | | X | X |
| Rubber tree | *Hevea brasiliensis* | | | X | |
| Rice | *Oryza sativa* | | X | X | |
| Oat | *Avena sativa* | | X | | |
| Bamboo | *Bambusa* spp. | | | X | |
| Begonia | *Begonia* spp. | X | | | |
| Eggplant | *Solanum melongena* | X | | | |
| Peanut | *Arachis hypogea* | X | | X | X |
| Coffee | *Coffea arábica* | X | | X | |
| Cocoa | *Theobroma cacao* | | X | X | |
| Zucchini | *Cucurbita pepo* | X | | | |
| She-oak | *Casuarina* spp. | | | X | |
| Camellia | *Camelia* spp. | X | | | |
| Sweet potato | *Ipomea batatas* | X | | | |
| Cinammon | *Cinnamomum zeylanicum* | | | X | |
| Sugar cane | *Sacharum officinarum* | X | X | | X |
| Safflower | *Carthamus tinctorius* | | X | X | |
| White onion | *Allium cepa* | X | X | | |
| Cedar | *Chamaecyparis* spp. | X | | | |
| *Citrus* plants | *Citrus* spp. | X | | X | X |
| Coconut tree | *Cocos nucifera* | | | X | |
| Cauliflower | *Brassica oleracea* var. *Botrytis* | | X | X | X |
| Carnation | *Dianthus caryophyllus* | X | X | X | |
| *Chrysanthemum* | *Chrysantemum morifolium* | X | | | |
| Chayote | *Sechium edule* | X | | | |
| Chili | *Capsicum annum* | X | X | | |
| Peach | *Prunus persica* | X | X | | |
| Epazote | *Chenopodium ambrisioides* | X | | | |
| Spinach | *Spinacea oleracea* | | | | X |
| Loofah | *Lufa cylindrica* | X | | | |
| Strawberry | *Fragaria* spp. | X | X | X | |
| White ash | *Fraxinus americana* | X | | | |
| Bean | *Phaseolus vulgaris* | X | X | X | |
| Gardenia | *Gardenia jasminoides* | X | | | |
| Chickpea | *Cicer arietium* | X | | | |
| Gladiolus | *Gladiolus* spp. | | | | |
| Guava | *Psidium guajava* spp. | X | | | |
| Broad bean | *Vicia faba* | X | | | |
| Fig | *Ficus carica* | | | X | |
| Mexican Yam | *Pachirizus angulatus* | X | | | |
| Lettuce | *Lactuca sativa* | X | X | X | |
| Lemmon | *Citrus limón* | | | | X |
| Maize | *Zea mays* | | X | X | X |
| Apple tree | *Malus* spp. | X | X | X | |
| Mango | *Manguifera indica* | | X | X | X |
| Daisy | *Aster* spp. | X | | | |
| Shasta Daisy | *Chrysantemum máximum* | X | X | | |
| Melon | *Cucumis melo* | X | X | X | X |
| Mint | *Mentha piperita* | X | X | X | |
| Yam | *Dioscorea* spp. | | X | | |
| Walnut tree | *Juglans regia* | X | | X | X |
| Prickly pear | *Opuntia* spp. | | | X | X |
| Okra | *Abelmoschus esculentus* | X | | | |
| Papaya | *Carica papaya* | X | | | |
| Potato | *Solanum tuberosum* | X | X | X | |
| Barnyard grass | *Echinocloa* spp. | | X | X | |
| Cucumber | *Cucumis sativus* | X | | | |
| Banana | *Musa* spp. | X | X | X | |
| Jamaica pepper | *Pimenta dioica* | | | X | |
| Pine | *Pinus* spp | | X | | |
| Mexican mountain pine | *Pinus hartwegii* | X | | | |
| Pineapple | *Ananas comunus* | X | X | X | X |
| Pummelo | *Citrus maxima* | | | | |
| Watermelon | *Citrullus lanatus* | X | | X | |
| White willow | *Salix alba* | X | | | |
| *Sorghum* | *Sorghum vulgare* | | X | | |
| Soy | *Glycine max* | | X | X | |

TABLE 1-continued

Crops affected by nematodes

| Common name | Scientific name | | | | |
|---|---|---|---|---|---|
| Tobacco | *Nicotiana tabacum* | | | X | X |
| Tomato | *Lycopersicon esculentum* | X | X | X | |
| Ground cherry | *Physalis* spp. | | X | X | |
| Common wheat | *Triticum aestivum* | | X | | |
| Trigo | Buckwheat | X | | | |
| Vine | *Vitis vinifera* | X | X | X | |
| Madagascar periwinkle | *Vinca rosea* | X | | | |
| African violet | *Saint paulina* spp. | X | | | |
| Carrot | *Daucus carota* | X | | | |

| Common name | Scientific name | *Radopholus* | *Hoplolaimus* | *Xiphinema* | *Ditylenchus* |
|---|---|---|---|---|---|
| Swiss chard | *Beta vulgaris* | | | | |
| Agave | *Agave atrovirens* | | X | X | |
| Avocado | *Persea americana* | | X | X | X |
| Garlic | *Allium sativum* | | | X | X |
| Alfalfa | *Medicago sativa* | | X | X | X |
| Cotton | *Gossypium hirsutum* | | X | X | |
| Sugar-apple | *Anona* spp. | | | X | |
| Rubber tree | *Hevea brasiliensis* | | | | |
| Rice | *Oryza sativa* | | X | X | |
| Oat | *Avena sativa* | | | | |
| Bamboo | *Bambusa* spp. | | | | |
| Begonia | *Begonia* spp. | | | | |
| Eggplant | *Solanum melongena* | | | | |
| Peanut | *Arachis hypogea* | | X | | |
| Coffee | *Coffea arabica* | | | | |
| Cocoa | *Theobroma cacao* | X | X | X | |
| Zucchini | *Cucurbita pepo* | | | | |
| She-oak | *Casuarina* spp. | | | X | |
| *Camellia* | *Camelia* spp. | | | | |
| Sweet potato | *Ipomea batatas* | | | | |
| Cinammon | *Cinnamomum zeylanicum* | | | X | |
| Sugar cane | *Sacharum officinarum* | | | X | |
| Safflower | *Carthamus tinctorius* | | | | |
| White onion | *Allium cepa* | | | | X |
| Cedar | *Chamaecyparis* spp. | | | | |
| *Citrus* plants | *Citrus* spp. | X | X | X | X |
| Coconut tree | *Cocos nucifera* | | | | |
| Cauliflower | *Brassica oleracea* var. *Botrytis* | | | X | X |
| Carnation | *Dianthus caryophyllus* | | | X | |
| *Chrysanthemum* | *Chrysantemum morifolium* | | | | |
| Chayote | *Sechium edule* | | X | | |
| Chili | *Capsicum annum* | | | X | X |
| Peach | *Prunus persica* | X | X | X | |
| Epazote | *Chenopodium ambrisioides* | | | | |
| Spinach | *Spinacea oleracea* | | | | |
| Loofah | *Lufa cylindrica* | | | | |
| Strawberry | *Fragaria* spp. | | X | X | X |
| White ash | *Fraxinus americana* | | | | |
| Bean | *Phaseolus vulgaris* | | X | X | |
| Gardenia | *Gardenia jasminoides* | | | | X |
| Chickpea | *Cicer arietium* | | X | | |
| Gladiolus | *Gladiolus* spp. | | | | X |
| Guava | *Psidium guajava* spp. | | | | |
| Broad bean | *Vicia faba* | | | | |
| Fig | *Ficus carica* | | | | |
| Mexican Yam | *Pachirizus angulatus* | | | | |
| Lettuce | *Lactuca sativa* | | | | |
| Lemmon | *Citrus limon* | | | | |
| Maize | *Zea mays* | | X | X | X |
| Apple tree | *Malus* spp. | | X | X | |
| Mango | *Manguifera indica* | | | X | |
| Daisy | *Aster* spp. | | | | |
| Shasta Daisy | *Chrysantemum maximum* | | | | |
| Melon | *Cucumis melo* | | | X | |
| Mint | *Mentha piperita* | | X | | |
| Yam | *Dioscorea* spp. | | | | |
| Walnut tree | *Juglans regia* | | | X | X |
| Prickly pear | *Opuntia* spp. | | | | |
| Okra | *Abelmoschus esculentus* | | | | |
| Papaya | *Carica papaya* | | | X | X |
| Potato | *Solanum tuberosum* | | X | X | X |
| Barnyard grass | *Echinocloa* spp. | X | X | X | X |
| Cucumber | *Cucumis sativus* | | | X | |

TABLE 1-continued

Crops affected by nematodes

| | | | | |
|---|---|---|---|---|
| Banana | *Musa* spp. | X | X | X |
| Jamaica pepper | *Pimenta dioica* | | | |
| Pine | *Pinus* spp | | X | |
| Mexican mountain pine | *Pinus hartwegii* | | | |
| Pineapple | *Ananas comunus* | | | X |
| Pummelo | *Citrus maxima* | X | | |
| Watermelon | *Citrullus lanatus* | | | X |
| White willow | *Salix alba* | | | |
| Sorghum | *Sorghum vulgare* | X | | X |
| Soy | *Glycine max* | | X | |
| Tobacco | *Nicotiana tabacum* | | X | X |
| Tomato | *Lycopersicon esculentum* | | X | |
| Ground cherry | *Physalis* spp. | | | |
| Common wheat | *Triticum aestivum* | | X | |
| Trigo | Buckwheat | | | |
| Vine | *Vitis vinifera* | | X | |
| Madagascar periwinkle | *Vinca rosea* | | | |
| African violet | *Saint paulina* spp. | | | |
| Carrot | *Daucus carota* | | | |

Sedentary endoparasitic nematodes are those that deform the roots of different crops due to inducing the overgrowth of the cells in the feeding site within which causes root galls (*Meloidogyne* spp.).

Migratory endoparasitic nematodes completely penetrate in the root of its host, traveling through the cortex and feeding on the cytoplasm of the cells, thus causing extensive destruction of tissues, and causing atrophy in the radicular system of plants (*Ditylenchus* spp., *Pratylenchus* spp., and *Radopholus* spp., among others).

Semiendoparasitic nematodes are deeply affixed to the host plant, leaving part of the body exposed to the outside. The juvenile are released to soil when hatching out, and subsequently they affix to the root of the plant (*Heterodera* spp., and *Punctodera* spp., among others).

Sedentary ectoparasitic nematodes only introduce the cephalic part of their body in the host plant, and usually do not become detached, except for reproduction. They oviposit directly in the soil (*Helicotylenchus* spp., *Tylenchorhinchus* spp., and *Criconemoides* spp., among others).

Migratory ectoparasites feed on a specific place during a short time and only introduce the stylet in the root of the plant. Some induce the formation of syncytia; a multinucleated hyperplastic cell where the nematode feeds (*Xiphinema* spp., *Longidorus* spp., and *Trichodorus* spp., among others).

Agriculture is the most important productive sector on most of the countries, where has a significant place in employment generation, the overall increase in agricultural incomes is a necessary condition for stimulating the growth of the entire economy, including non-agricultural sectors that sell their products and services to the rural population.

Mexico has a national territory of 198 million hectares, of which 145 million are dedicated to livestock, this is why agriculture represents an important productive sector, with a contribution of 4% to the national gross domestic product, is a core activity in rural areas, in which a highly significant part of the national population still inhabits.

The climatic differences between different regions of the world and even between regions in each country are significant in terms of climate and ecosystem, so pest control in crops in those regions is vital for farmers to be competitive nationally and internationally.

Therefore, it is necessary to have a method for pest control that works in different conditions of the soil and ambient, which also do not affect the quality of the product or the health of producers and/or consumers; in the present invention is disclosed the use of a fungus for nematode control, with outstanding efficacy and efficiency and inexpensive.

OBJECT OF THE INVENTION

The present invention relates to the use of the biologically pure strain *Paecilomyces carneus*, as well as compositions, methods and use for the prevention and/or control and/or eradication of phytoparasitic nematodes, migratory and sedentary endoparasites belonging to families Anguinidae, Aphelenchidae, Aphelenchoididae, Criconematidae, Dolichodoridae, Hemicycliophoridae, Heteroderidae, Hoplolaimidae, Iotonchidae, Neotylenchidae, Pratylenchidae, Sphaerulariidae, Tilenchidae, and Tylenchulidae: Suborder Tylenchina; Longidoridae: Suborder Dorylaimina; Trichodoridae: Suborder Diphtherophorina, that infect and/or infest crops in order to obtain safe quality products for animal and human consumption.

DETAILED DESCRIPTION OF THE INVENTION

Figure 1:
FIG. 1. *Meloidogyne* spp. parasitized by *Paecilomyces carneus* strain IE-431.

The present invention relates to the use and application of one or more cells of *Paecilomyces carneus* for the control and/or prevention and/or eradication of phytoparasitic nematodes from the groups of migratory endoparasites and/or sedentary endoparasites of the families Anguinidae, Aphelenchidae, Aphelenchoididae, Criconematidae, Dolichodoridae, Hemicycliophoridae, Heteroderidae, Hoplolaimidae, Iotonchidae, Neotylenchidae, Pratylenchidae, Sphaerulariidae, Tilenchidae, and Tylenchulidae: Suborder Tylenchina; Longidoridae: Suborder Dorylaimina; Trichodoridae: Suborder Diphtherophorina, that infect and/or infest cropland.

The *Paecilomyces carneus* strains IE-412, IE-416, IE-418, IE-419, IE-431, IE-451, and IE-452 are deposited, preserved and stored in the ceparium of fungi of the Instituto de Ecologia A.C. (INECOL), production and/or isolation and/or preservation of such strains is performed by breeding them on a solid culture medium consisting of at least one source of nitrogen and/or at least one carbon source and/or one or more mineral salts and/or at least a suitable carrier and/or at least one antibiotic agent and/or at least one growth promoting agent. The incubation temperature of the fungus in the culture medium is about 13-37° C.

Propagation and reproduction of the fungus consist in the inoculation of cells in compositions of solid or liquid mediums comprising one or more amino-acids, and/or one or more long-chain carbohydrates, and/or one or more mineral salts, and/or one or more vehicles, and/or one or more antibiotic agents, and/or one or more buffers in sufficient quantities. The culture is fixed or static and with uninterrupted oxygenation in a percentage between 40% and 90% of oxygen content to allow the optimum development of the fungus *Paecilomyces carneus*.

The mechanism of action of *Paecilomyces carneus* is characterized by the production of specific enzymes that allow it to degrade the cuticle and penetrate to the interior of the nematode in any of its stages (juvenile and adult eggs, among others), where it grows and reproduces until causing the death of the different taxonomic groups of phytoparasitic nematodes.

The 1E-418 strain of *Paecilomyces carneus* is characterized by having the DNA nucleotide sequence coded as follows:

```
GGGATCATTACCGAGTTTACAACTCCCAAACCCCTGTGAACTTATACCA

TTTACTGTTGCTTCGGCGGGTCACGGCCCCGGGGAAGGACAGCGGTCGCC

GTCAGGCCTCAGCTGCCCGCCCCCGGAAACAGGCGCCCGCCGGGGAACTC

AAACTCTTCTGTATTTCTTTATCTAATATATACTGTCTGAGTAAAAACTA

AAATGAATCAAAACTTTCAACAACGGATCTCTTGGTTCTGGCATCGATGA

AGAACGCAGCGAAATGCGATAAGTAATGTGAATTGCAGAATTCAGTGAAT

CATCGAATCTTTGAACGCACATTGCGCCCGCCAGTATTCTGGCGGGCATG

CCTGTTCGAGCGTCATTTCAACCCTCAAGTCCCTGTGGACTCGGTGTTG

GGGACCGGCGAGACAGCCGCGGATCTTCTTCCGCAGCGAGTCGCCGCCC

CCAAATGACTTGGCGGCCTCGTCGCGGCCCTCCTCTGCGTAGTATAGCAC

ACCTCGCAACAGGAGCCGGCGAATGGCCACTGCCGTAAAACCCCCCAAC

TTTTTCAGAGTTGACCTCGAATCAGGTAGGAATACCCGCTGAACTTAAGC

ATATCA (SEQ ID NO: 1).
```

The IE-418 strain of *Paecilomyces carneus* has the following structural features:

Mycelium with radial growth, upright conidiophores, in PDA grows 12 mm in 10 days, white hairy dusty mycelium, in EMA grows from 9 to 11 mm in ten days. In both media it stains dark green 29F8 the back of the culture medium plate according to the 1961's Farver i Farver color chart from Wanscher and Kornerup. White mycelium, filamentous dusty texture. In oatmeal agar (OA) it grows from 18 to 20 mm in ten days. Mycelium with dusty texture due to the sporulation, which turns from white to slightly pinkish 7A2 in OA in a time greater than 55 days after inoculation. It stains slightly the culture medium in the back of the case with grayish yellow 3C3 or 3C4 irregularly after 35 days, and in the oldest parts with olive green 3E7. Bottle-shaped conidiogenic cells, tapering towards the tip in a very thin neck, monophialidic, or in well-defined verticillia of 2-5 cells, although groups of three cells predominate, with a minimum length of: 7.2-8.8 µm; the more frequent length is: 9.6-10.4 µm and the greater length is between: 11-14.4 µm. The width is 1.6-2.4 µm. Subglobose conidia, ellipsoidal to spheric, equinulated, arranged in chains. The spores are 2.4-4.0 µm long and 1.6-2.4 µm. width. In 5 mm discs, the sporulation is $25 \times 10^6$ spores.

The IE-418 strain from *Paecilomyces carneus* product of the present invention, is characterized by having the ability to infect and/or infest phytoparasitic nematodes from groups of: migratory endoparasites, and/or sedentary endoparasites, and/or semiendoparasites, and/or migratory ectoparasites, and/or sedentary ectoparasites from the classification according to the molecular analysis proposed by De Ley P. and Blaxter. M. in 2004, from the following families: Anguinidae, and/or Aphelenchidae, and/or Aphelenchoididae, and/or Criconematidae, and/or Dolichodoridae, and/or Hemicycliophoridae, and/or Heteroderidae, and/or Hoplolaimidae, and/or Iotonchidae, and/or Neotylenchidae, and/or Pratylenchidae, and/or Sphaerulariidae, and/or Tilenchidae, and/or Tylenchulidae: Suborder Tylenchina; and/or Longidoridae: Suborder Dorylaimina; and/or Trichodoridae: Suborder Diphtherophorina.

During the investigation of the use and application of the IE-431 strain of *Paecilomyces carneus* in the control, and/or prevention, and/or eradication of phytoparasitic nematodes, migratory and sedentary endoparasites, semiendoparasites, and migratory and sedentary ectoparasites it was established that said strain, even when infects such nematodes, requires at least 15 days for the infection without controlling and/or eradicating the nematodes, except in the case of *Meloidogyne* spp. Surprisingly and unexpectedly it was found that the IE-418 strain of *Paecilomyces carneus* infests and/or infects the phytoparasitic nematodes in less than 72 hours, controlling and eradicating the above-mentioned families of nematodes.

A first stage of evaluation of the effectiveness and efficiency of the IE-418 strain of *Paecilomyces carneus*, was carried out placing cells (conidiospores, and/or blastospores, and/or hyphal fragments) in a suspension of *Paecilomyces carneus* IE-418 in contact with migratory and sedentary endoparasitic nematodes, semiendoparasites and migratory and sedentary ectoparasites, among which are: *Meloidogyne* spp., *Pratylenchus* spp., *Radopholus* spp., *Helicotylenchus* spp., *Criconemoides* spp.; *Hoplolaimus* spp.; *Xiphinema* spp. and, separately the same nematodes were placed in contact with *Paecilomyces carneus* strain IE-431.

The results of this first stage for the IE-431 strain of *Paecilomyces carneus* were the following:

1. The viability of the juvenile and adult egg masses of nematodes of genus *Meloidogyne* spp. is reduced.
2. At 24 hours after being brought into contact, the fungus germinated and penetrated to the host.
3. At 72 hours the mycelium was found in development both inside and outside of the egg masses and females of *Meloidogyne* spp.
4. At 120 hours the fungus completely invaded the whole egg mass and the interior of the females of *Meloidogyne* spp. (FIG. 1).

The results of this first stage for the IE-431 strain of *Paecilomyces carneus* with *Pratylenchus* spp., *Hoplolaimus* spp., and *Criconemoides* spp. were the following:

1. At 120 hours after being brought into contact, some fungal spores germinating on the cuticle of the nematode were seen.
2. At 15 days, the mycelium had an incipient development outside the nematode, so it is not possible to control or to eradicate the same.

Figure 2:
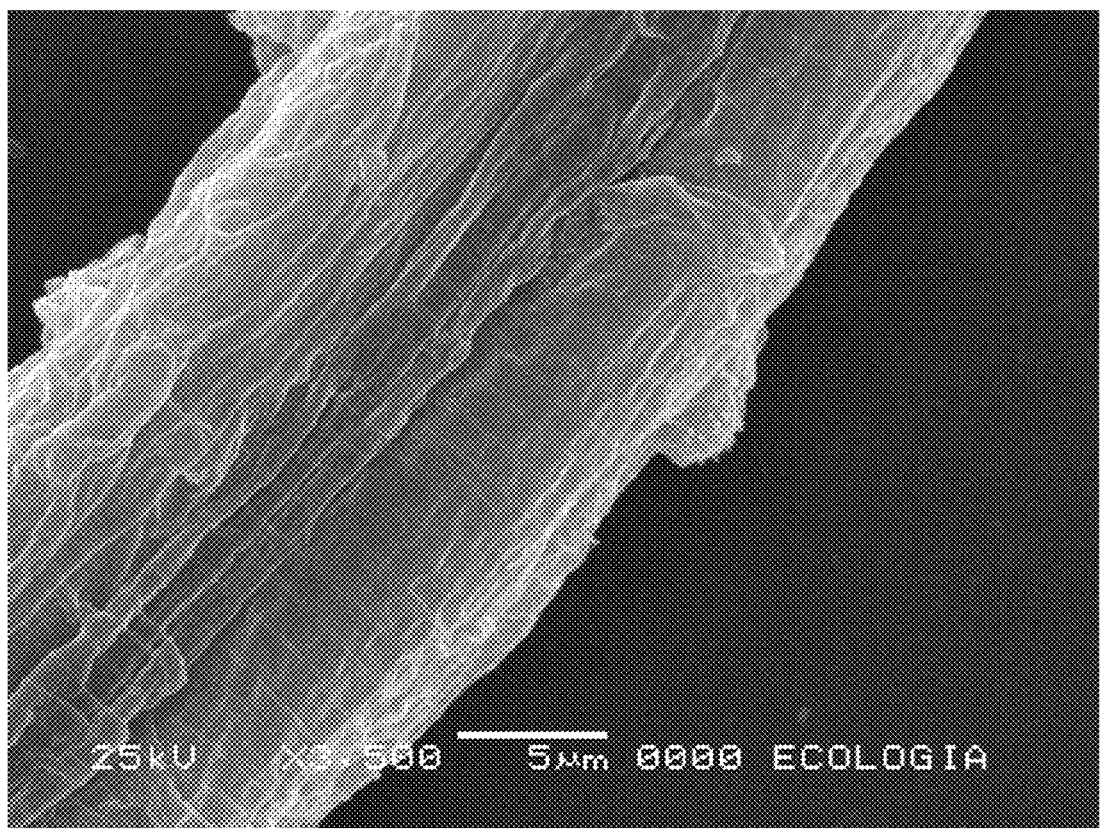
FIG. 2. Development of *Paecilomyces carneus* strain 418 over *Pratylenchus* spp. at 72 hrs.
Figure 3:
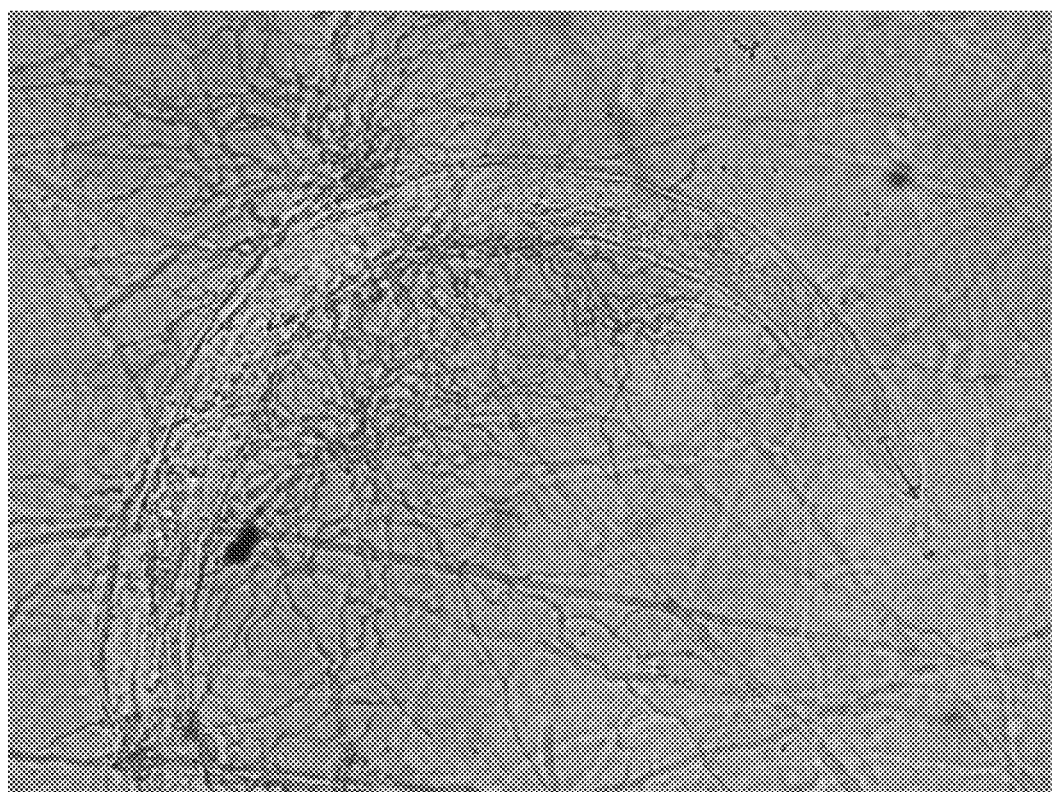
FIG. 3. Development of *Paecilomyces carneus* strain 418 over *Pratylenchus* spp. at 120 hrs.

The results of this first stage for the IE-431 strain of *Paecilomyces carneus* were the following:

1. At 48 hours after being brought into contact, the fungus germinated and penetrated to the nematode.
2. From 72 (FIG. 2) to 120 hours (FIG. 3) the mycelium was found in development both inside and outside the nematode, which indicates the potential for control and/or eradication thereof.

Figure 4:
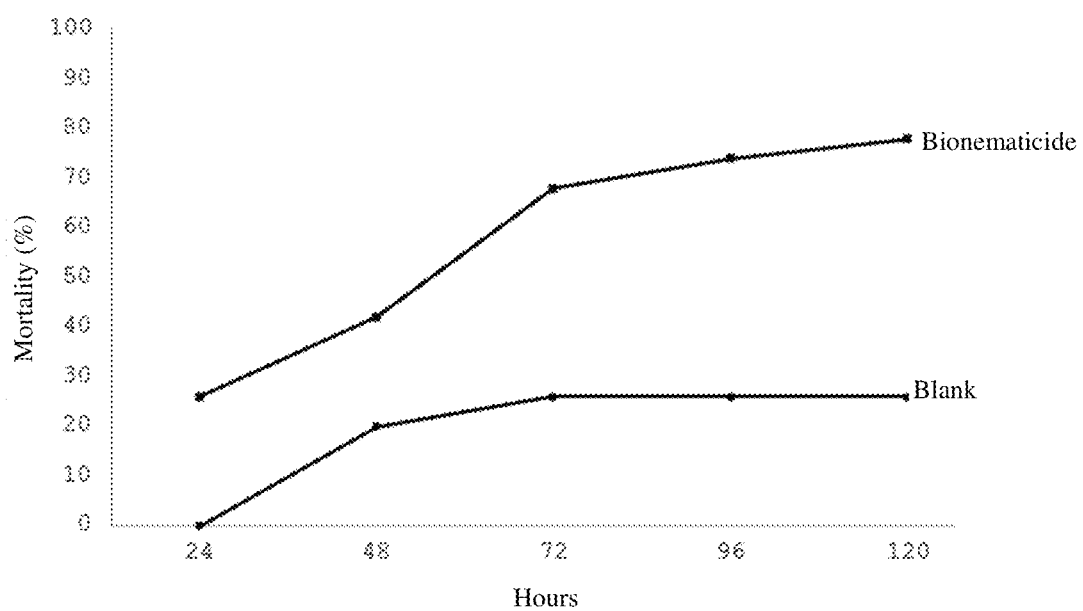
FIG. 4. Pathoenicity plot for *Paecilomyces carneus* strain 418 over *Hoplolaimus* spp.

In a second stage, it was carried out the assessment of pathogenicity expressed as % mortality for IE-418 strain of *Paecilomyces carneus* in contact with ectoparasitic nematodes (FIG. 4):

1. 2% mortality was obtained in individuals of *Hoplolaimus* spp. at 24 hours of exposition to *Paecilomyces carneus* IE-418.
2. At 24 hrs of exposition to the fungus a 68% mortality was found for *Hoplolaimus* spp. At 120 hrs of exposition to the fungus a 78% mortality was found for individuals of
3. *Hoplolaimus* spp.
4. On the contrary, in the blank treatment it was found only 26% individuals of *Hoplolaimus* spp. dead at 120 h after the start of the experiment.

Figure 5:
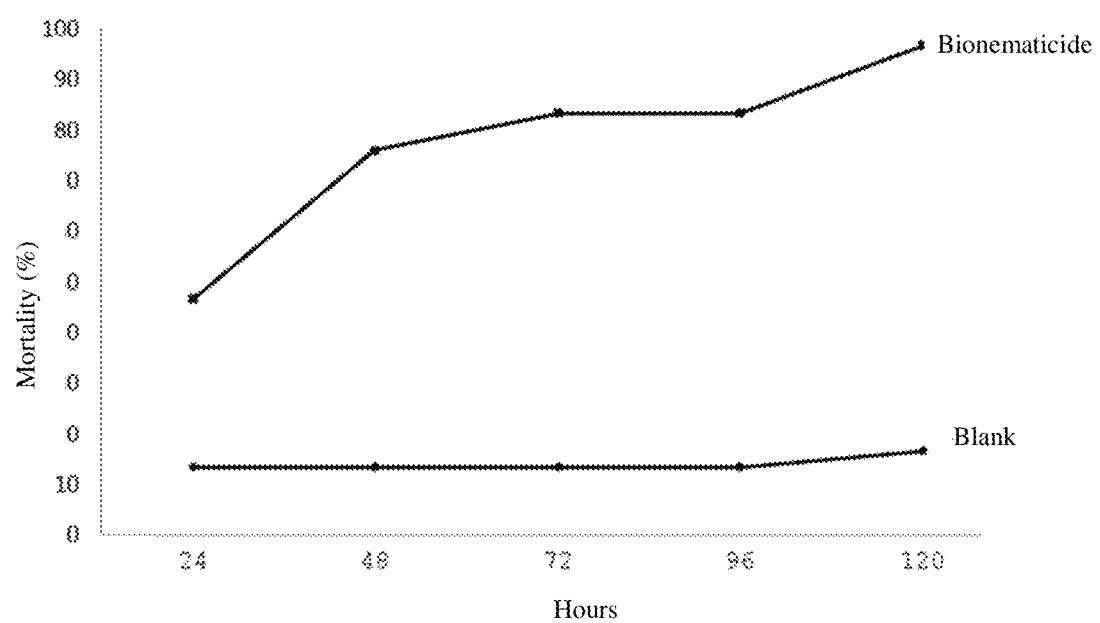
FIG. 5. Pathoenicity plot for *Paecilomyces carneus* strain 418 over *Criconemoides* spp.

In the assessment of pathogenicity expressed as mortality for IE-418 strain of *Paecilomyces carneus* in contact with *Criconemoides* spp. (FIG. 5.)

1. 46% mortality of individuals of *Criconemoides* spp. was obtained at 24 hrs of exposure to IE-418 strain of *Paecilomyces carneus*.
2. At 72 hrs of exposure to IE-418 strain of *Paecilomyces carneus* more than 80% individuals of *Criconemoides* spp. were found parasited with the fungus.
3. Finally at 120 hrs after having infected the nematodes *Criconemoides* spp. with IE-418 strain of *Paecilomyces carneus* 96% individuals were found dead, and with visible sporulation.
4. On the contrary, in blank treatment, it was not seen evidence of mycelium and only a 16.6% mortality was found.

In a third stage, the application procedure of *Paecilomyces carneus* was combined with crop rotation and application of *Beauveria bassiana* and *Lecanicillium lecanii* for combating in parallel other existing crop pests such as: thrips (Order Thysanoptera), whitefly (Order Hemiptera), greenfly *Aphis* spp. (Order Hemiptera) (which may affect the plant since its early stages, which significantly affect production), and the chafer, *Macrodactylus* spp. (Order Coleoptera), which is an omnivorous insect and can destroy a crop in a few days; and diseases caused by Helotiales, such as *Botrytis fabae* (chocolate spot disease), and/or *B. cinerea* (grey rot), and/or diseases caused by Uredinales, such as *Uromyces* spp., and/or *Puccinia* spp., and/or *Tranzschelia* spp. (rusts), which producers of various crops can no longer control with chemicals sold in the market.

For the prevention, and/or control, and/or eradication of nematodes and also said pests and diseases, *Lecanicillium lecanii* was used in early stages of plant growing, applied separately or in combination with *Paecilomyces carneus* in the soil.

Surprisingly, the results obtained were the significant reduction of thrips, whitefly and greenfly pests, and an almost complete reduction of chocolate spots. With regard to the rust, the crop remains clean until the production of sheaths and filling thereof in the case of broad bean, i.e., when the seed is ripe and ready to be harvested.

Additionally, *Beauveria bassiana* was applied for the control of *Macrodactylus* spp. In 2 or more days such pest starts to die and diminish significantly the culture damage. To obtain better results, the fungus *Beauveria bassiana* is applied during farm work to affect before the larval stage and thus reduce the population.

The results obtained were an increment in the yield of wide bean plants in plots treated with biological control, in comparison with plots with chemical control (50% less sheaths) and the blank plot.

Therefore, the strain IE-418 of *Paecilomyces carneus* is characterized by reducing the nematode population since the first application with total efficacy reached in three to five days for nematodes of Families Anguinidae, and/or Aphelenchidae, and/or Aphelenchoididae, and/or Hemicycliophoridae, and/or Heteroderidae, and/or Hoplolaimidae, and/or Iotonchidae, and/or Neotylenchidae, and/or Pratylenchidae, and/or Sphaerulariidae, and/or Tilenchidae, and/or Tylenchulidae: Suborder Tylenchina; and/or Longidoridae: Suborder Dorylaimina; and/or Trichodoridae: Suborder Diphtherophorina. However, the strain IE-431 fails to carry out its nematicide action in most of the above-mentioned phytoparasitic nematodes, but it is extremely effective and specific in endoparasitic and/or semiendoparasitic nematodes of Family Heteroderidae.

The present invention discloses a method for isolation, and/or preservation, and/or massive reproduction of *Paecilomyces carneus*, as well as the use, and/or application thereof for the control, and/or prevention, and/or eradication of nematodes infecting and/or infesting areas for cultivation of Swiss chard, agave, avocado, garlic, alfalfa, cotton, sugar-apple, rubber tree, myrtle, rice, oat, baricoco, bamboo, begonia, egg plant, broccoli, peanut, coffee, cocoa, star apple, zucchini, pumpkin, courgette, bitter berry, she-oak, camellia, sweet potato, cinnamon, sugar cane, starfruit, apricot, safflower, barley, onion, cedar, citron, plumb, citrus plants, coconut tree, cabbage, cauliflower, carnation, chrysanthemum, ice-cream bean, chicozapote, pea, chili, peach, epazote, spihach, loofah, raspberry, strawberry, ash, bean, gardenia, chick pea, gladiolus, pomegranate, guava, wide bean, fig, Mexican yam, lettuce, lime, lemon, maize, mamee, tangerine, apple tree, mango, daisy, shasta daisy, melon, quince, mint, blackberry, yam, orange, nectarine, walnut tree, prickly pear, okra, papaya, potato, barnyard grass, cucumber, pear, banana, pepper, pine, pineapple, dragon fruit, pummelo, watermelon, white willow, satsuma, sorghum, soy, tobacco, tomato, ground cherry, grapefruit, wheat, vine, Madagascar periwinkle, African violet, carrot, yellow mombin, yellow chapote, cherimoya, soursop, paradise plum, cashew tree, melon, loquat, cucumber, persimmon, rose apple, watermelon, yellow sapote, white sapote, black sapote, sugar apple, between other crops in which this type of parasite spreads.

The compositions with cells of *Paecilomyces carneus* can be developed for application in the form of suspension, granules, powder, lyophilized, pellets, controlled release forms, ecological pump, gels, jellies, pastes, capsules, immobilized cells, emulsion, micro-emulsion, solution, and/or combinations thereof.

EXAMPLES

Nematicide compositions of *Paecilomyces carneus* obtained are provided below in a descriptive and not restrictive way:

Example 1: Composition 1 of *Paecilomyces carneus* Strain 418

| COMPONENT | AMOUNT |
|---|---|
| *Paecilomyces carneus* cells | $0.5 \times 10^7$ cells/mL |
| Carrot juice | 80-100 mL |
| Yeast | 0.1-5.0 g/L |
| Ampicillin | 500 mg |
| Water | q.s. 1000 mL |

Example 2: Composition 2 of *Paecilomyces carneus* Strain 418

| COMPONENT | AMOUNT |
|---|---|
| *Paecilomyces carneus* cells | $0.5 \times 10^7$ cells/mL |
| Oat | 20-50 g/L |
| Yeast | 0.1-5.0 g/L |
| Chloramphenicol | 1000 mg |
| Water | q.s. 1000 mL |

Example 3: Composition 3 of *Paecilomyces carneus* Strain 418

| COMPONENT | AMOUNT |
|---|---|
| *Paecilomyces carneus* cells | $0.5 \times 10^7$ cells/mL |
| Oat | 5-25 g/L |
| Yeast | 0.1-5.0 g/L |
| Chloramphenicol | 1000 mg |
| Water | q.s. 1000 mL |

Example 4: Composition 4 for Isolation and Preservation of *Paecilomyces carneus* Strain IE-418

| COMPONENT | AMOUNT |
|---|---|
| *Paecilomyces carneus* cells | $0.5 \times 10^7$ cells/mL |
| Carrot | 50-160 g/L |
| Potato | 20-50 g/L |
| Chloramphenicol | 1000 mg |
| Water | q.s. 1000 mL |

Example 5: Composition 5 for Isolation and Preservation of *Paecilomyces carneus* Strain IE-418

| COMPONENT | AMOUNT |
|---|---|
| *Paecilomyces carneus* cells | $0.5 \times 10^7$ cells/mL |
| Rye | 15-50 g/L |
| Chloramphenicol | 1000 mg |
| Water | q.s. 1000 mL |

The application method of one or more compositions of *Paecilomyces carneus* generally consists in:

One or more applications of the composition(s) of *Paecilomyces carneus* to the soil at least 10 days prior to sowing for disinfecting it. The number of applications depends on the species of the phytoparasitic nematodes and its population density.

In the case of crops whose sowing is carried out from tubers, bulbs, rhizomes, corms, among others, the application consists in immerse them in the composition(s) for at least one hour before the sowing.

For the transplantation of shrub and/or tree crops, the application is performed directly to the root of the plant and/or to the soil where they will be sown.

In the case of crops planted by seeds, the composition(s) are applied in the furrow before laying the seed and/or directly in the seed shortly before sowing.

Optionally and without limitations, the application of the composition(s) is performed after sowing and/or during the growing of the crop.

During and/or after the harvest, and/or during the culture rotation period, and/or the soil rest the application of the composition(s) is done to the soil in order to prevent new infestations and/or control and/or eradicate the phytoparasitic nematodes population remaining. This practice prepares the soil for the next growing cycle.

Complementarily, it can be added to said composition one or more biological agents for nematode control, selected from the following: *Bacillus thuringiensis, Bacillus thuringiensis* ATCC 55273, *Bacillus firmus* CNCMI-1582, *Sphingobacterium* strain *spiritivorum, Corynobacterium paurometabolum, Arthrobotrys* spp., *Pasteuria penetrans* 98-35, *Streptomyces dicklowii, Stevia rebaudiana, Streptomyces rubrogriseus, Pochonia chlamydosporia, Monacrosporium ullum, Bacillus amyloliquefaciens, Verticillium chlamydosporium* CC 334168, *Bacillus subtillis* No. DSM17231, and/or *Bacillus licheniformis* DSM 17236, *Verticillium chlamydosporium, Paecilomyces lilacinus, Paecilomyces fumosoroseus, Paecilomyces lilacinus* 251, *Paecilomyces lilacinus* 252, *Paecilomyces lilacinus* 253, and *Paecilomyces lilacinus* 254, *Rhizoctonia solani* AG-4, *Fusarium oxysporum, Pythium* sp., *Phytophthora nicotiana, Verticillium dahliae, Paecilomyces cicadae, Sphingobacterium spiitivorum* C-926, and/or *Corynebacterium paurometabolum* C-924 *Paecilomyces carneus* strain IE-431, and/or *Beauveria bassiana*, and/or *Lecanicillium lecanii*, and/or *Calcarisporium* spp., and/or combinations thereof.

In a comprehensive manner, the present invention provides the following advantages:

1. Biological method for rational management of nematode pests in crops.
2. Quality improvement of soil for cultivation.
3. Remediation of soil damaged by chemical agents like pesticides.
4. Obtaining high-quality agricultural products and forestry resources.
5. Improvement in crop and/or forest resources yield.
6. Favors the provision of macro elements such as phosphorus in the soil to the plant and improves soil fertility. Its phosphate solubilization efficacy is comparable to that of *Penicillium* spp. and *Aspergillus* spp.

7. The eradication of phytoparasitic nematodes is seen from the first application in less time compared to other control methods.

8. Nematicide compositions obtained are safe for humans, plants, and animals.

9. It allows the combination with other control methods such as crop rotation, soil rest, among others.

10. Is a sustainable method of prevention, and/or control, and/or eradication of phytoparasitic nematodes, easy to manage and apply.

11. It is an economic and profitable method in the short, medium and long term.

12. The specificity is due to the production of specific enzymes that attack the phytoparasitic nematodes without affecting the free-living nematodes beneficial to the agricultural system.

IE-418 strain was also deposited in the Chilean Collection of Microbial Resources (CChRGM) with the access number RGM2140 Date Dec. 13, 2013 said fungus is selected from *Botrytis fabae*, *B. cinerea*, *Uromyces* spp., *Puccinia* spp., *Tranzschelia* spp., *Rhizoctonia* spp., and *Fusarium* spp.

2. The method according to claim 1, wherein said phytoparasitic nematode is selected from *Aphelenchus* spp., *Aphelencoides* spp., *Pratylenchus* spp., *Radopholus* spp., *Helicotylenchus* spp., *Criconema* spp., *Tylenchulus* spp., *Nacobbus* spp., *Rotylenchus* spp., *Rotylenchulus* spp., *Tylenchus* spp., *Ditylenchus* spp., *Criconemoides* spp., *Hoplolaimus* spp., *Xiphinema* spp., *Longidorus* spp., *Trichodorus* spp., *Discocriconemella* spp., *Hemicycliophora* spp., *Paratylenchus* spp., and *Tylenchorhinchus* spp.

3. The method according to claim 1, wherein said method comprises contacting a pest or fungus with the composition, and wherein said composition further comprises *Lecanicillium lecanii* and/or *Beauveria bassiana*.

4. The method according to claim 1, wherein the plant is a coffee tree and the method comprises contacting the nematode or fungus on the coffee tree with a composition comprising *Paecilomyces carneus* in combination with *Lecanicillium lecanii*, *Calcarisporium arbuscula*, and *Calcarisporium ovalisporum*.

The invention claimed is:

1. A method of controlling and/or eradicating a pest, phytoparasitic nematode, or fungus on plants or in soil comprising contacting a pest, a nematode, or a fungus with a composition comprising *Paecilomyces carneus*, wherein, said phytoparasitic nematode is selected from Anguinidae, Aphelenchidae, Aphelenchoididae, Criconematidae, Dolichodoridae, Hemicycliphoridae, Hoplolaimidae, Iotonchidae, Neotylenchidae, Pratylenchidae, Sphaerulariidae, Tylenchidae, Tylenchulidae: Suborder Tylenchina; Longidoridae: Suborder Dorylaimina; and Trichodoridae: Suborder Diphtherophorina;

said pest is selected from Thysanoptera, Hemiptera, and Coleoptera; and

5. The method according to claim 4, wherein the phytoparasitic nematode is a gall-inducer nematode.

6. The method according to claim 1, wherein the plant is a potato with black scurf disease caused by a fungus, and wherein the method comprises contacting the fungus with a composition comprising *Paecilomyces carneus* in combination with *Lecanicillium lecanii*, *Calcarisporium arbuscula*, and *Calcarisporium ovalisporum*.

7. The method according to claim 6, wherein the fungus is *Rhizoctonia solani*.

8. The method according to claim 1, wherein the composition further comprises one or more biological control agents selected from *Bacillus thuringiensis*, *Bacillus firmus*, *Sphingobacterium spiritivorum*, *Corynebacterium paurometabolum*, *Arthrobotrys* spp., *Pasteuria penetrans*, *Strep-* tomyces dicklowii, Stevia rebaudiana, Streptomyces rubrogriseus, Pochonia chlamydosporia, Monacrosporium ullum, Bacillus amyloliquefaciens, Verticillium chlamydosporium, Bacillus subtillis, Bacillus licheniformis, Verticillium chlamydosporium, Paecilomyces lilacinus, Paecilomyces fumosoroseus, Paecilomyces lilacinus, Rhizoctonia solani, Fusarium oxysporum, Pythium sp., Phytophthora nicotiana, Verticillium dahliae, Paecilomyces cicadae, Corynebacterium paurometabolum, Lecanicillium lecanii, Beauveria bassiana, Calcarisporium arbuscula, Calcarisporium ovalisporum*, plant extracts used for pest control, and combinations thereof.

9. The method according to claim 1, wherein the *Paecilomyces carneus* is *Paecilomyces carneus* having a genetic sequence of SEQ ID NO: 1.

* * * * *

UNITED STATES PATENT AND TRADEMARK OFFICE
CERTIFICATE OF CORRECTION

PATENT NO.         : 9,867,378 B2
APPLICATION NO.    : 14/652271
DATED              : January 16, 2018
INVENTOR(S)        : Gloria Luz Laura Carrion Villarnovo et al.

Page 1 of 1

It is certified that error appears in the above-identified patent and that said Letters Patent is hereby corrected as shown below:

In the Claims

Column 16, Line 6, Claim 2, delete "Aphelencoides" and insert -- Aphelenchoides --

Column 16, Line 12, Claim 2, delete "Tylenchorhinchus" and insert -- Tylenchorhynchus --

Column 16, Line 66, Claim 8, delete "Corynobacterium" and insert -- Corynebacterium --

Column 17, Line 4, Claim 8, delete "subtillis," and insert -- subtilis, --

Signed and Sealed this
Tenth Day of April, 2018

Andrei Iancu
*Director of the United States Patent and Trademark Office*